US007038106B1

(12) United States Patent
Kaiser et al.

(10) Patent No.: US 7,038,106 B1
(45) Date of Patent: May 2, 2006

(54) DETECTION OF NEURAL ACTIVITY

(75) Inventors: Kim Kaiser, Milngavie (GB); Philippe Rosay, Glasgow (GB); James Douglas Armstrong, Glasgow (GB)

(73) Assignee: The University Court of the University of Glasgow, Glasgow (GB)

( * ) Notice: Subject to any disclaimer, the term of this patent is extended or adjusted under 35 U.S.C. 154(b) by 0 days.

(21) Appl. No.: 09/701,996

(22) PCT Filed: Jun. 7, 1999

(86) PCT No.: PCT/GB99/01786

§ 371 (c)(1),
(2), (4) Date: Apr. 30, 2001

(87) PCT Pub. No.: WO99/64859

PCT Pub. Date: Dec. 16, 1999

(30) Foreign Application Priority Data

Jun. 6, 1998 (GB) .................................... 9812127

(51) Int. Cl.
*G01N 33/00* (2006.01)
*A01K 67/00* (2006.01)
*A61K 49/00* (2006.01)

(52) U.S. Cl. ............................... 800/8; 800/3; 424/9.1; 424/9.2

(58) Field of Classification Search .................... 800/8, 800/3; 424/9.1, 9.2
See application file for complete search history.

(56) References Cited

U.S. PATENT DOCUMENTS 5,714,666 A   2/1998  Pritchett et al. ............... 800/2
5,777,195 A   7/1998  Fienberg et al. ............... 800/2

FOREIGN PATENT DOCUMENTS

EP    0 713 092 A1    5/1996
WO    WO93/15184      5/1993

OTHER PUBLICATIONS

Duffy et al.; Adrenergic Calcium Signaling in Astrocyte Networks within the Hippocampal Slice; The Journal of Neuroscience, Aug. 1995, 15(8): 5535-5550.*
O'Brochta et al.; Recent Developments in Transgenic Insect Technology; Parasitology Today vol. 13, No. 3, 1997; pp. 99-104.*
Cameron. Recent Advances in Transgenic Technology. Molec. Biotech. 1977, vol. 7, pp. 253-265.*
Sigmund. Viewpoint: Are Studies on Geneically Altered Mice Out of Control? Arterioscler. Thromb. Vasc. Biol. 2000, vol. 20, pp. 1425-1429.*
Nieman. Transgenic Farm Animals Get Off the Ground. Transgenic Research. 1998, vol. 7, pp. 73-75.*
Bal et al., J. Neurophysiology, 77(6):3145-3156, Jun. 1997.*
Izu, Leighton T., *A Class of Parametrically Excited Calcium Oscillation Detectors*, Biophysical Journal, vol. 68, pp. 1621-1629 (Apr. 1995).
Chay, Teresa Ree, *Electrical bursting and luminal calcium oscillation in excitable cell models*, Biological Cybernetics, pp. 419-431 (1996).
Fan, Yin-Shui, et al., *Generation of periodic and chaotic bursting in an excitable cell model*, Biological Cybernetics, vol. 71, No. 5, pp. 417-421 (1994).
Rosay, Philippe, et al., *Cell-type specific calcium signalling in a Drosophila epithelium*, Journal of Cell Science, vol. 110, pp. 1683-1692 (1997).
Dani et al., "The triggering of astrocytic calcium waves by NMDA-induced neuronal activation", *Ciba Found Symp.*, 188:195-205 (1995).
Grapengiesser et al., "Glucose-Induced Oscillations of Cytoplasmic $Ca^{2+}$ in the Pancreatic $\beta$-Cell", *Biochemical and Biophysical Research Communications*, 151(3):1299-1304 (1988).
Grapengiesser, "Glucose Induces Cytoplasmic $Na^+$ Oscillations in Pancreatic $\beta$-Cells", *Biochemical and Biophysical Research Communications*, 226:830-835 (1996).
Gu et al., "Pharmacological Analysis of Heartbeat in *Drosophila*", *Journal of Neurobiology*, 28(3):269-280 (1995).
Rohr et al., "Multiple Site Optical Recording of Transmembrane Voltage (MSORTV) in Patterned Growth Heart Cell Cultures: Assessing Electrical Behavior, with Microsecond Resolution, on a Cellular and Subcellular Scale", *Biophysical Journal*, 67:1301-1315 (1994).
Wang et al., "Mechanism of synchronized $Ca^{2+}$ oscillations in cortical neurons", *Brain Research*, 767:239-249 (1997).
Woods et al., "Repetitive transient rises in cytoplasmic free calcium in hormone-stimulated hepatocytes", *Nature*, 319: 600-602 (1986).

* cited by examiner

*Primary Examiner*—Joseph Woitach
(74) *Attorney, Agent, or Firm*—Dann, Dorfman, Herrell and Skillman; Kathleen D. Rigaut

(57) ABSTRACT

The present invention discloses an in situ method of screening a compound for pharmacological activity comprising the steps of detecting an initial pattern of neural activity in brain tissue, adding the compound to the brain tissue and detecting a resulting pattern of neural activity, and observing the pharmacological activity of the compound on neural activity by comparing the initial pattern of intracellular neural activity with the resulting pattern of neural activity.

21 Claims, 16 Drawing Sheets

DETECTION OF NEURAL ACTIVITY

RELATED APPLICATIONS

Figure 1A:
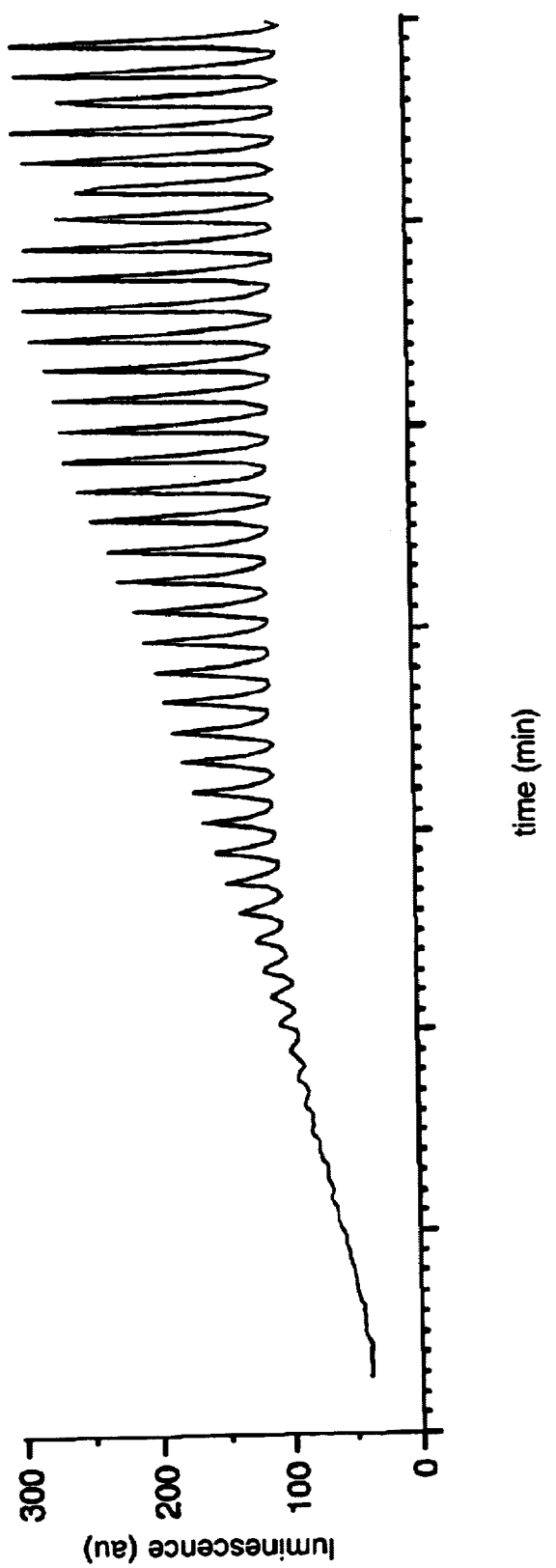

This application claims priority from International Patent Application No. PCT/GB99/01786, filed on Jun. 7, 1999, which in turn claims priority from Great Britain Application No. GB9812127.0, filed on Jun. 6, 1998, both in English, the disclosures of which are incorporated herein by reference in their entireties.

The present invention relates to an in situ insect brain tissue assay, particularly suited for Dipteran brain tissue and to uses of such an assay.

In a multicellular organism, cell communication is essential to regulate the different activities of specialised tissues. In all animal cells, there are conserved intracellular second messenger pathways. Of these, calcium is an important second messenger. In nerve cells, muscle and other cells, modulation of intracellular calcium activity from typical resting levels of 100 nM regulates many short and long-term processes. Measurement of calcium is thus of great importance in understanding both normal function and disease states, and drugs that modulate calcium signalling have proved of clinical significance in treating a wide range of disorders.

The present inventors have demonstrated the utility of a transgenic aequorin expression system in the genetic model organism Drosophila; Rosay et al (1997).

Using the GAL4/UAS enhancer trap system, based upon synthetic P-element transposons, the present inventors showed that it was possible to express apoaequorin specifically in defined subsets of cells of the Malpighian tubule, and that incubation of the freshly-dissected tubule tissue in coelenterazine was sufficient to reconstitute functional aequorin; Rosay et al (1997).

The present invention is based on the surprising discovery by the inventors that using the technique described above oscillations of intracellular calcium concentration are observed in the intact Drosophila brain. These oscillations are long period, cell-type-specific, endogenous, robust and synchronous, a combination of features that is to the best of the present inventor's knowledge unprecedented. Since calcium oscillations in this system appear to reflect an oscillation of neural activity, other means by which neural activity can be monitored may be expected to reveal the same basic process.

Calcium oscillations of similar period have been seen in certain vertebrate systems, though largely in the context of single cells rather than intact tissues, for example cultured hippocampal neurons (Jaffe, 1994; Seymour-Laurent, 1995; Ogden, 1996) and cortical neurons (Robinson, et al, 1993; Wang and Gruenstein, 1997) in the case of the nervous system. Some cell lines representatives of vertebrate peripheral tissues display oscillations in the 5 mHz range under hormonal stimulation, for example hepatocytes treated with oxytocin, vasopressin, angiotensin-II or noradrenaline (Woods et al, 1986). Individual pancreatic beta cells treated with glucose show large amplitude oscillations of cytoplasmic sodium and calcium (Grapengiesser et al, 1988; Grapengiesser, 1996). There has been little direct evidence for similar oscillations occurring in situ, however, except in hippocampal slices, where it appears to be confined to astrocytes rather than neurons (Dani, 1995; Duffy, 1995). The present inventors are aware of no reports concerning oscillations of similar nature in any insect nervous system.

In a first aspect the present invention provides an in situ method of screening a compound for a pharmacological activity which comprises the steps of:
a) detecting an initial pattern of neural activity in brain tissue;
b) adding the compound to the brain tissue and detecting a resulting pattern of neural activity; and
c) observing the pharmacological activity of the compound on neural activity by comparing the initial pattern of intracellular neural activity with the resulting pattern of neural activity.

An advantage of the present invention is that the present method is performed on intact tissues rather than cultured cells, arguably providing a truer reflection physiologically of the effects any particular reagent may have on neural function. In situ is taken to apply to tissue which remains in an organism being tested or to tissue which has been excised from an organism prior to testing.

It is to be understood that the term "neural activity" includes all measurable aspects of neural function that depend upon, give rise to, or occur in parallel with changes in intracellular calcium concentration. Typically, the "neural activity" may be detected as a pattern of intracellular calcium oscillation.

It is to be understood that the term "pharmacological activity" includes all activities whether of benefit or otherwise to an organism. Thus, the activity may be associated with a therapeutic activity, or alternatively the activity may be harmful or toxic to the organism e.g. biocidal.

The present assay, as applied to Drosophila brain tissue, can be used directly to screen for chemical agents with pharmacological or insecticidal activity. Oscillation of neural activity may be detected directly or indirectly by a range of methods; including but not restricted to: a) transgenic apoaequorin; b) other methods that monitor intracellular calcium concentration; c) other methods that monitor the operation of intracellular calcium signalling pathways; d) methods that monitor the operation of other types of signalling pathway; e) methods that monitor neuronal electrical potentials.

For example fluorescent probes (such as fura-2, indo-1, quin-2) show a spectral response upon binding calcium and it is then possible to detect changes in intracellular free calcium concentrations using fluorescence microscopy, flow cytometry and fluorescence spectroscopy. Most of these fluorescent indicators are variations of the nonfluorescent calcium chelators EGTA and BAPTA (Cobbold and Rink, 1987).

New fluorescent indicators for calcium called "cameleons" may also be used and are genetically encoded without cofactors and are targetable to specific intracellular locations. These so-called "cameleons" consist of tandem fusions of a blue-or cyan-emitting mutant of the green fluorescent protein (GFP), calmodulin, the calmodulin-binding peptide M13, and an enhanced green- or yellow-emitting GFP. Binding of calcium makes calmodulin wrap around to M13 domain, increasing (Miyawaki et al 1997) or decreasing (Romoser et al 1997) the fluorescence resonance energy transfer between flanking GFPs.

Additionally, potentiometric optical probes may be used. Potentiometric optical probes measure membrane potential in organelles and in cells. In conjunction with imaging techniques, these probes can be employed to map variations in membrane potential along neurons and among cell populations with high spatial resolution and sampling frequency (Rohr & Salzberg 1994).

By way of non-limiting example the present inventors have used the fruit fly (Drosophila) as a model for the presently described method and have detected intracellular calcium levels by expression of apoaequorin in the Drosophila brain under control of the yeast transcription factor, GAL4.

The Drosophila P[GAL4] enhancer-trap system is used both for the visualisation of particular classes of cells, and to provide a means of manipulating those cells in the living organism (Armstrong, 1997). Insertion of the P[GAL4] transposon occurring in the vicinity of a genomic transcriptional enhancer leads to expression of the yeast transcriptional activator GAL4 in a pattern reflecting that of the nearby enhancer.

By placing the calcium reporter aequorin under GAL4-control, the present inventors have established a system within which oscillating calcium concentrations can be detected non-invasively and with cell-type specificity in the intact Drosophila brain. As here described, oscillations have been detected in the mushroom bodies, brain centres for olfactory associative learning and memory and for mate preference. Mushroom bodies or analogous structures are found in all insects. In principle, the same approach will be applicable to oscillating activity in any cell type.

Detection may be performed on a whole live organism. A small part of the cuticle of the head may be removed so as to allow entry of any necessary reagents such as coelenterazine (for an aequorin expression system). Mutant organisms which possess a relatively permeable and/or translucent cuticle may also be used. Alternatively, brain tissue may be dissected out and reagents such as coelenterazine added thereto.

For the example of the aequorin expression system in the Drosophila brain, calcium oscillation becomes detectable soon after addition of coelenterazine, reaches full amplitude within one hour, and may last for 15 hours or more. Detection may be carried out using a CCD camera, or with a luminometer, or with any other light detection system.

Once an initial pattern of neural activity, eg. intracellular calcium oscillation has been detected, the compound to be screened may be added and its pharmacological activity on neural activity observed. The compound may include natural or synthetic compounds.

The pharmacological activity may manifest itself in a number of ways. For example, the compound may result in a cessation of the neural activity for a period of time, or variation in the pattern of activity or both. Such variations may include increases/decreases in an amplitude of oscillation, as well as alterations in the frequency and/or wave pattern observed.

Since an initial pattern of neural activity is detected, it is possible to ascertain whether the compound acts in an agonistic or antagonistic manner. That is, whether the compound subsequently increases or decreases the frequency/amplitude/degree of neural activity.

The method finds particular application in the screening of compounds which might perturb or otherwise alter the natural neural activity of the brain. The alteration may be as a direct result of the compound being screened on calcium dynamics, or the compound may affect a different pathway, such as a sodium or potassium channel, and have a secondary or resulting effect on calcium dynamics.

The method described herein finds particular application in the development of pesticides, by determining the activity of potential pesticidal compounds to a pest's nervous system, such as an insect nervous system.

The method described herein may also lead to the development of new drugs or new applications for existing drugs which are shown to have a pharmacological activity on neural tissue. Such drugs include calcium channel blockers, anticholinesterases, respiratory stimulants, antihypertensives, anti-Parkinson disease drugs, anti-Alzheimer disease drugs, anti-anginals; and anti-arrhythmics.

The assay may also be used to screen for environmental toxicants that perturb or otherwise alter neural activity, for example insecticides in crops, soil or water run-off from fields.

The discovery of calcium oscillation in the insect brain has also lead to further applications.

In a further aspect the present invention provides a method for detecting a calcium signalling mutant organism, the method comprising detecting a pattern of intracellular calcium oscillation in brain tissue of a test organism and comparing this with a pattern of intracellular calcium oscillation in neural tissue of a non-mutant organism.

Said mutants may display abnormal oscillatory activity.

Such a method may be used to screen for naturally occurring or induced mutations that perturb calcium dynamics and may lead to the discovery of new genes the products of which might be novel targets for the classes of drugs mentioned previously, or in the development of pesticides.

In a yet further aspect the present invention also provides a method for assessing an effect of an exogenous gene on the pattern of intracellular calcium oscillation in neural tissue, the method comprising detecting a pattern of intracellular calcium oscillation in neural tissue of an organism expressing the exogenous gene and comparing said pattern with a pattern of intracellular calcium oscillation in neural tissue of an organism without said exogenous gene.

The exogenous gene may be transiently expressed or the organism made transgenic for the particular exogenous gene. The exogenous gene may be of any origin; in particular of human or animal origin and may be chosen with an expectation that it may perturb or otherwise alter endogenous calcium signalling in the nervous system. Compounds may then be tested for their effect on calcium signalling in the expression background of the foreign gene.

Additionally it may be possible to combine the two above approaches. For example, a particular gene may be identified in humans as being potentially relevant to normal neurological functioning. A mutant Drosophila may be generated or be available which is dysfunctional for the Drosophila equivalent of this gene. The human gene is then expressed in the mutant Drosophila and compounds tested for their effect on calcium oscillation in the background of human gene expression.

Although exemplified above in relation to Drosophila and expression of the aequorin gene using the GAL4/UAS expression system, such a technique may be easily extended to other organisms which display endogenous oscillations of neural activity in the brain, and to alternative means of detecting neural activity as mentioned above (e.g. calcium and potentiometric dyes).

For example, other insect species may be made transgenic for the aequorin gene using appropriate transposon based technologies. Additionally apoaequorin may be expressed transgenically under the control of cell or tissue-specific promoters, either directly or via a system such as the GAL4/UAS system, or ubiquitously and non-selectively, by use of heat-shock, actin or similar promoters.

The aequorin gene may also be expressed by transient (non germ-line) transformation for example with an infectious agent such as a baculovirus vector system in insects and adenovirus systems in vertebrate systems.

Other animals may be made transgenic for the aequorin gene using appropriate germ-line transformation technologies, for example injection of apoaequorin expression constructs into fertilised oocytes, or ES cell transformations that are now routine in mouse and sheep.

The general approach could be extended to the neural tissue of any insect, for example insects which are considered pests and for which control thereof is necessary. Such pests include *Dictyoptera* (cockroaches); *Isoptera* (termites); *Orthoptera* (locusts, grasshoppers and crickets); *Diptera* (house flies, mosquito, tsetse fly, crane-flies and fruit flies); *Hymenoptera* (ants, wasps, bees, saw-flies, ichneumon flies and gall-wasps); *Anoplura* (biting and sucking lice); *Siphonaptera* (fleas); and *Hemiptera* (bugs and aphids), as well as arachnids such as *Acari* (ticks and mites).

Figure 1:
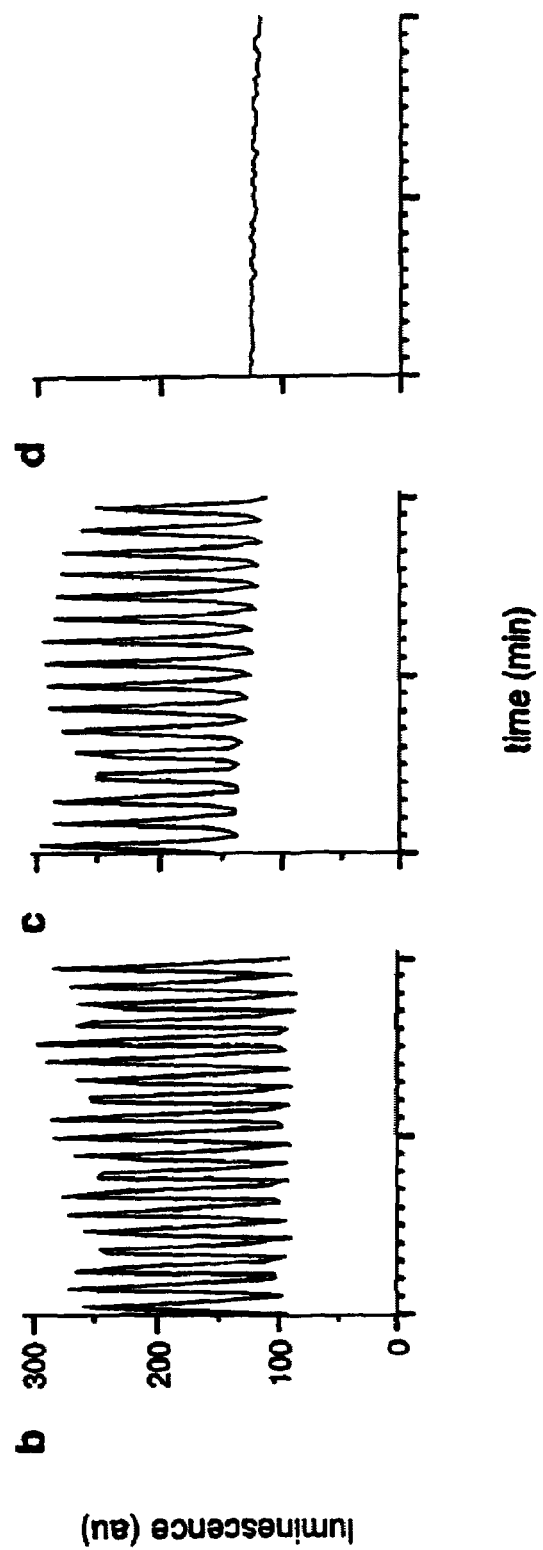
Figure 1:
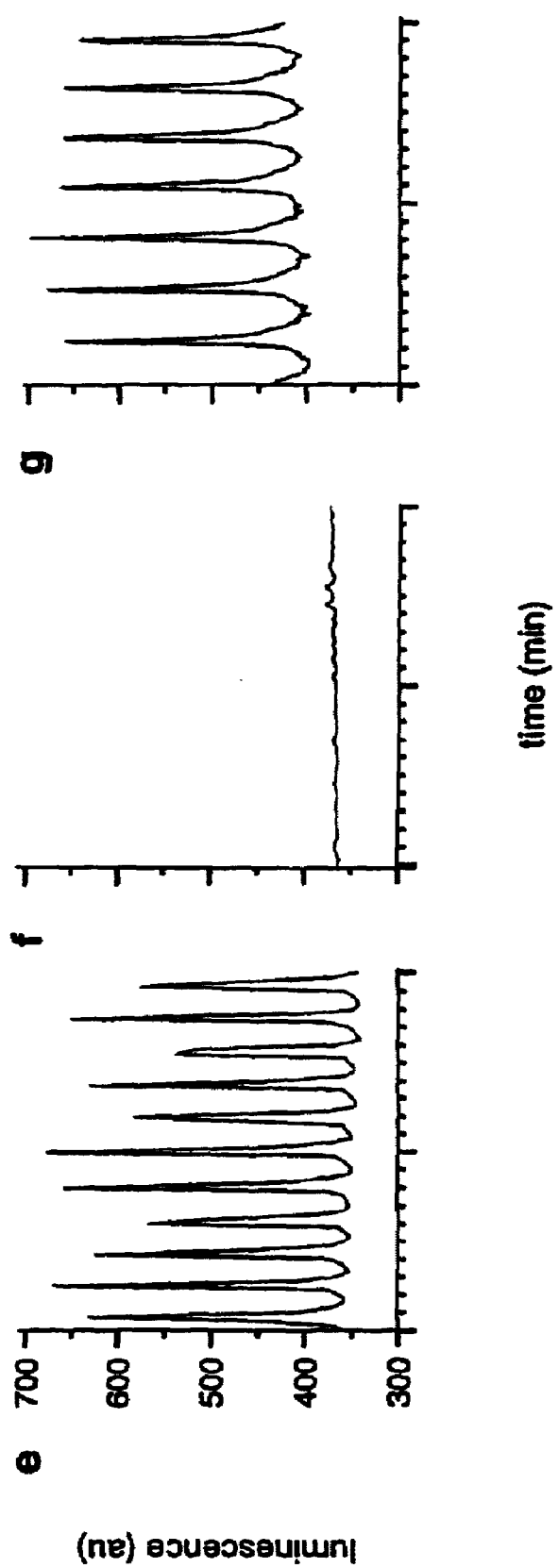

The present invention will now be further described by way of reference to the following non-limiting examples, wherein:

FIG. 1 shows luminometer traces of aequorin activity in the mushroom bodies of *Drosophila*. Luminescence is given in cps×$10^{-1}$ (a) 103Y-aeq adult brain from time of coelenterazine addition; (b) 117Y-aeq, adult brain; (c) 30Y-aeq, adult brain; (d) 30Y-aeq, HU ablated adult brain; (e) 117Y-aeq, whole fly; (f) 117Y-aeq, early pupal brain; (g) 117Y-aeq, late pupal brain.

Figure 2:
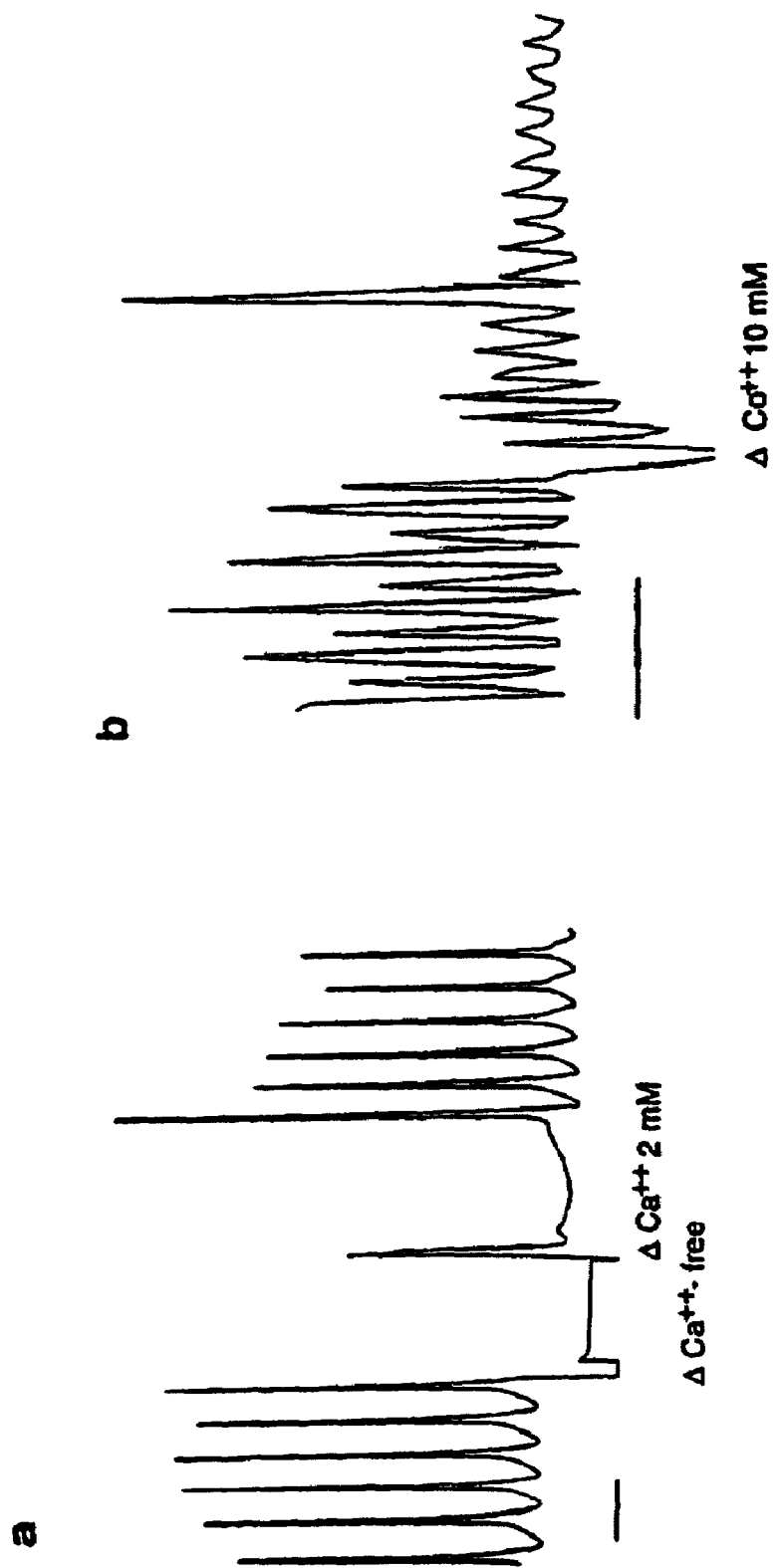
Figure 2:
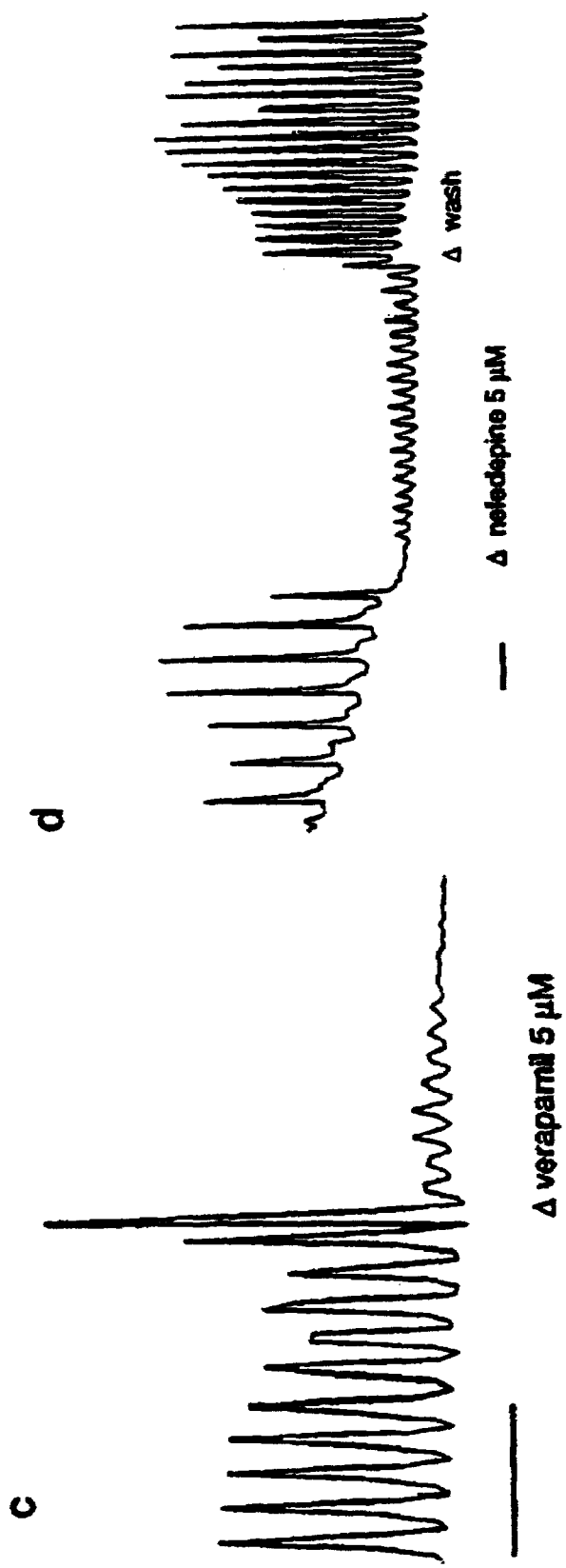
Figure 2:
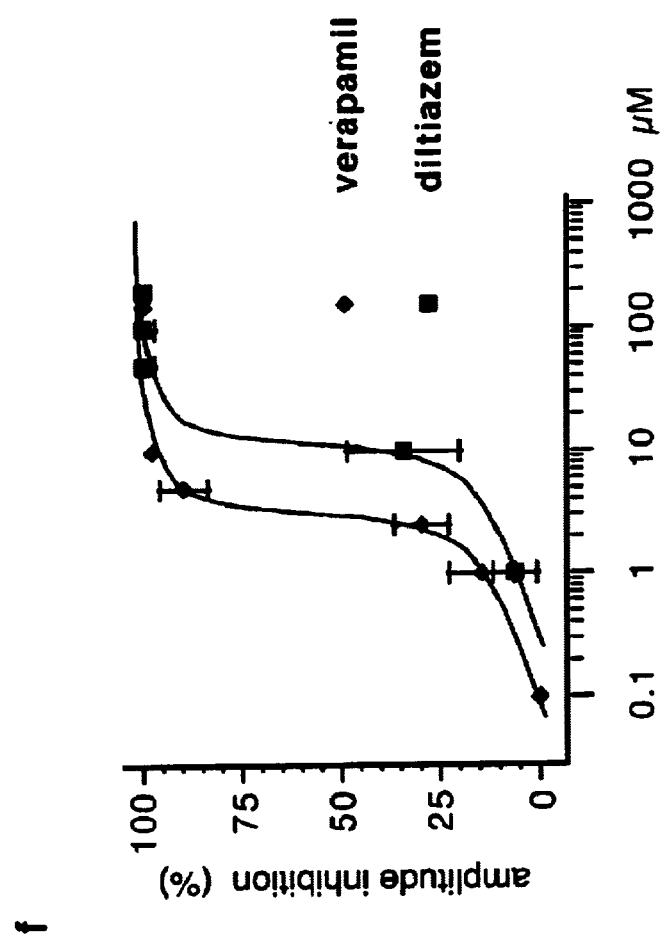
Figure 2:
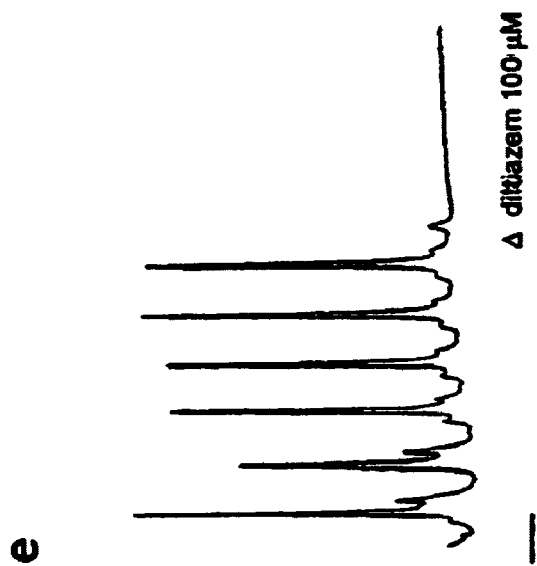

FIG. 2 shows calcium channel pharmacology. Representative traces of 117Y-aeq adult brains. Horizontal bar, 5 min. Effect of (a)Calcium-free Ringer's solution, (b) cobalt, (c) verapamil, (d) nifedipine and (e) diltiazem (f) Dose responses for verapamil (phenylalkylamine) and diltiazem (benzothiazepine), chemically independent blockers of L-type calcium channels.

Figure 3A:
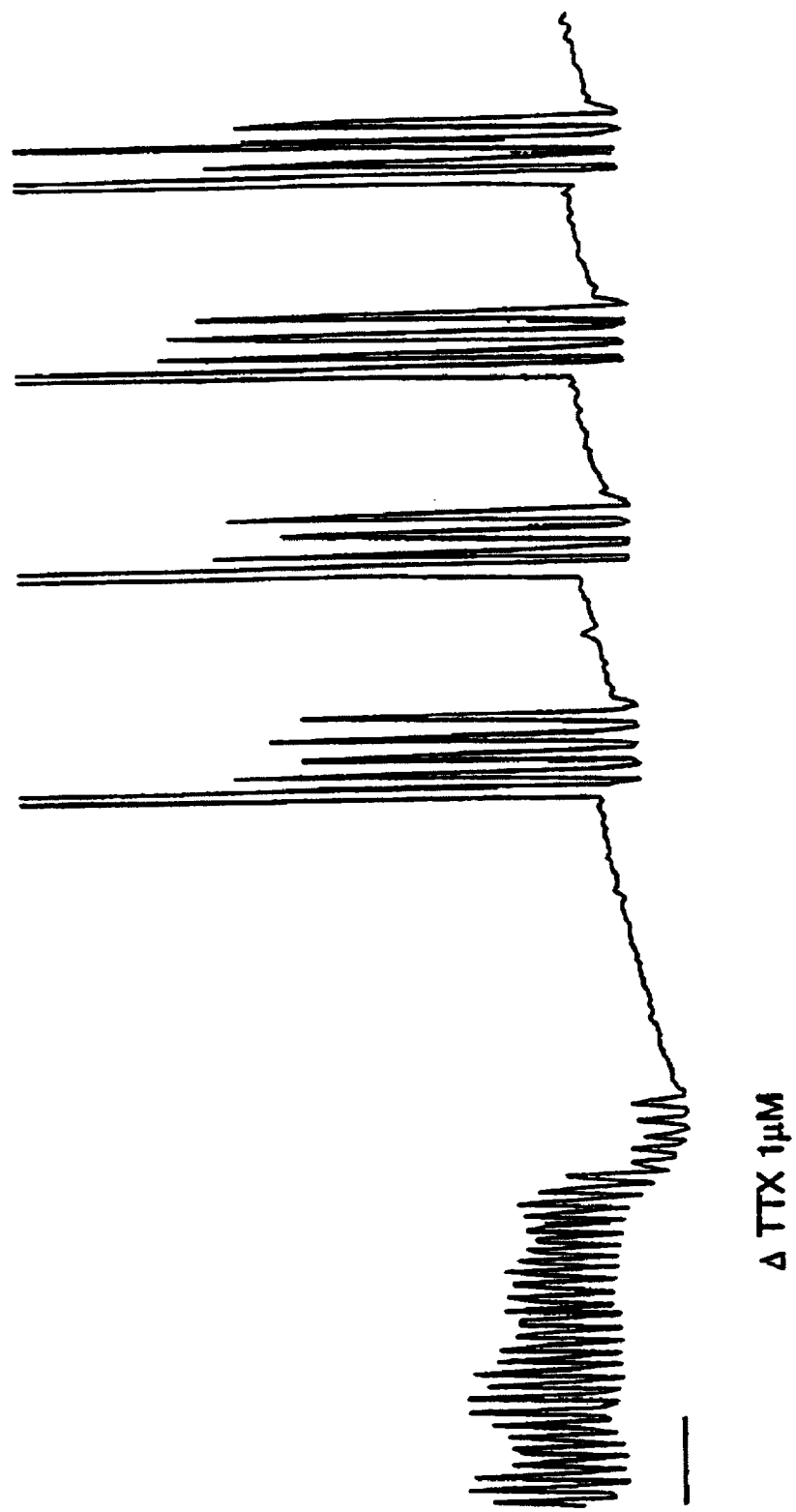
Figure 3B:
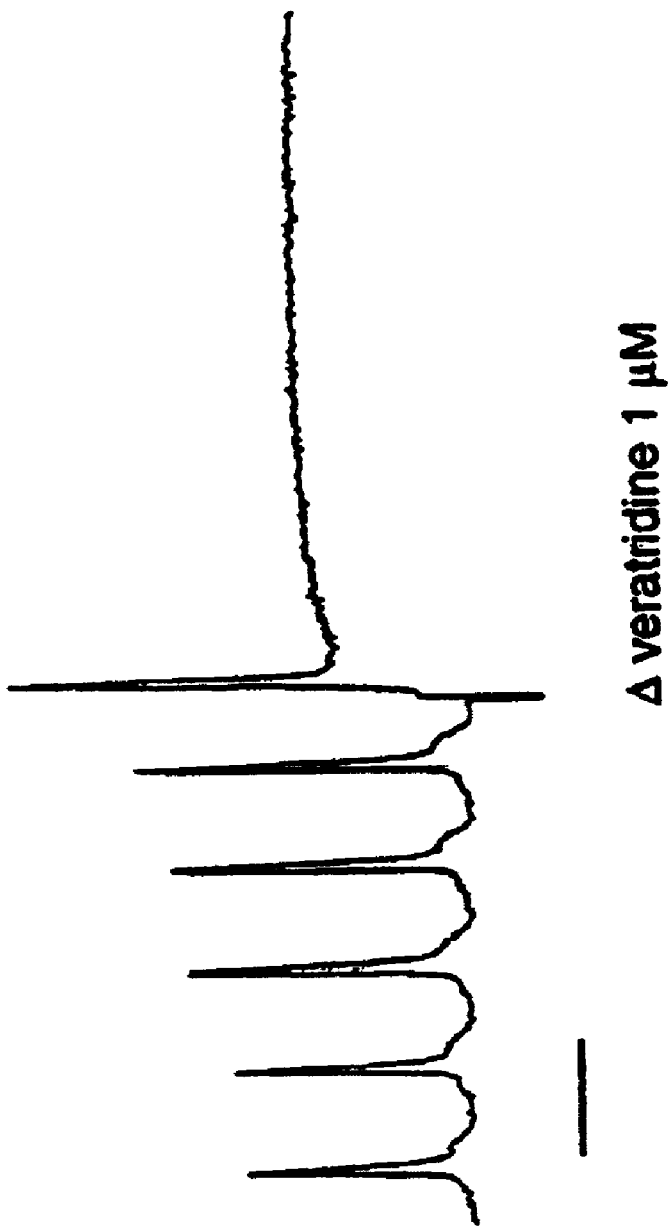

FIG. 3 shows an effect on calcium signalling of modulators of voltage gated sodium channel. Horizontal bar, 5 min. Effect of a) tetrodotoxin (TTX), b) veratridine treatment of a 117Y-aeq adult brain. TTX is an inhibitor of voltage gated sodium channels. Veratridine is a sodium channel opener.

Figure 4A:
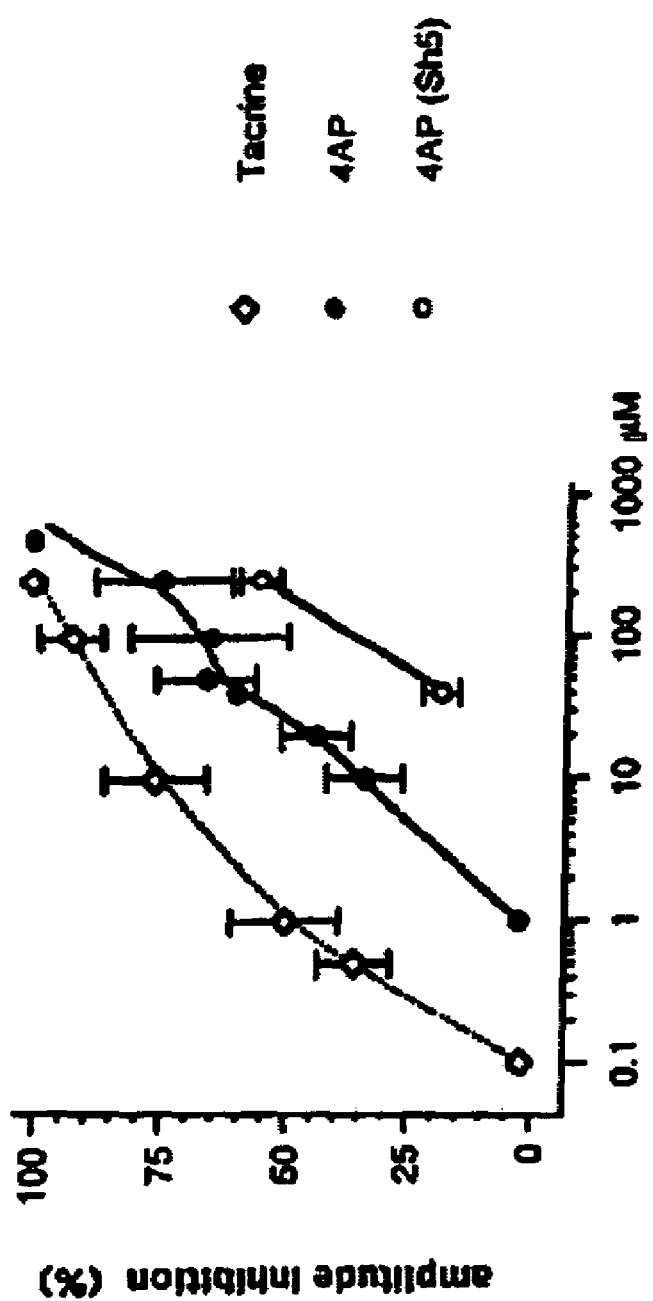
Figure 4B:
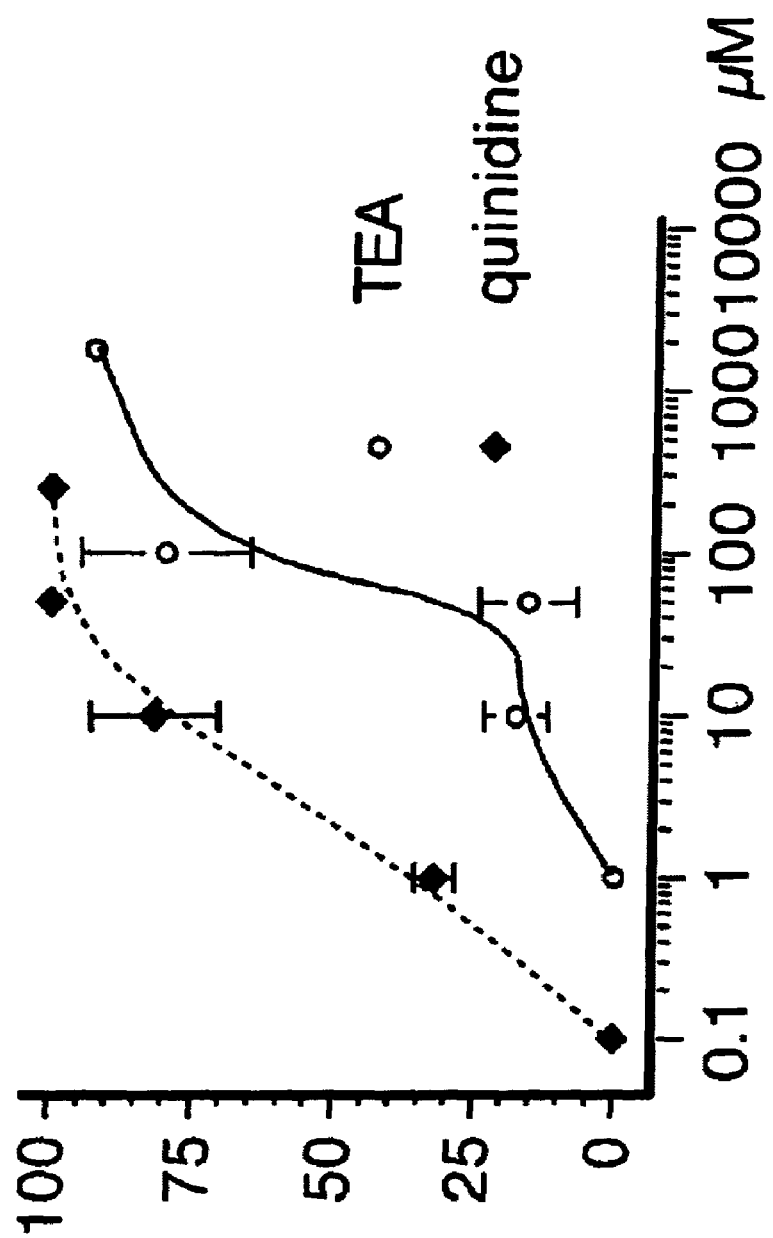
Figure 4:
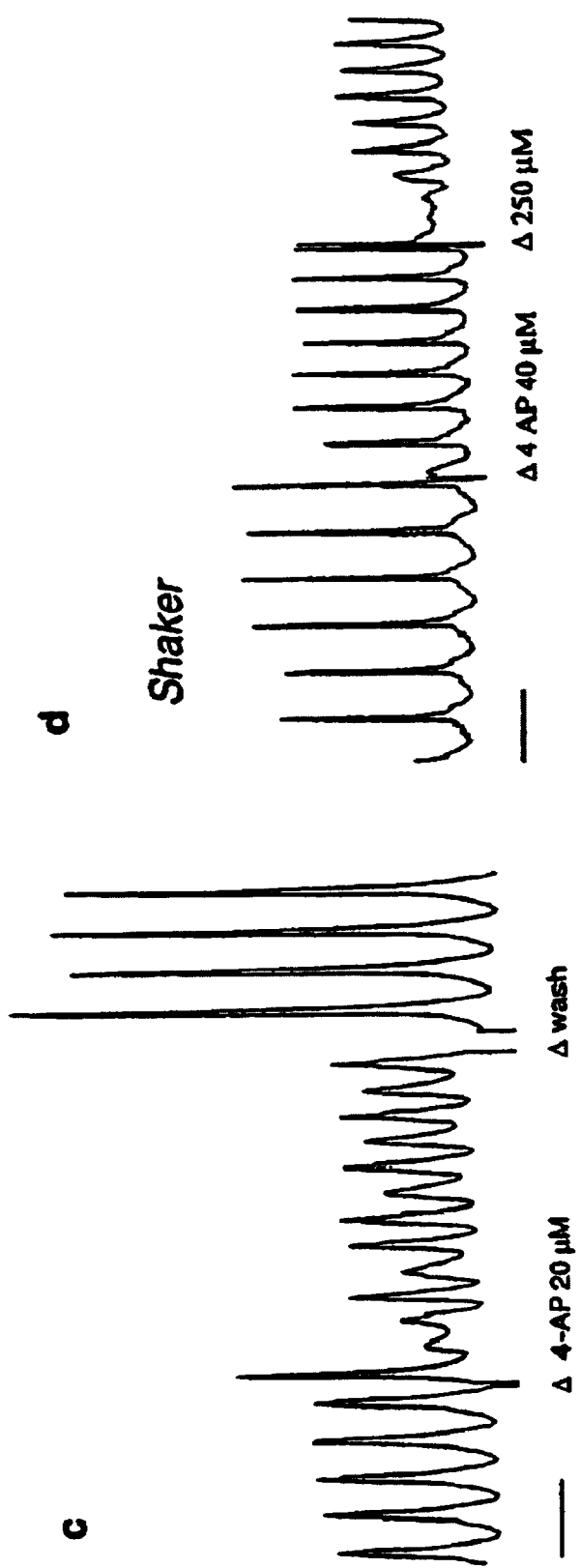
Figure 4:
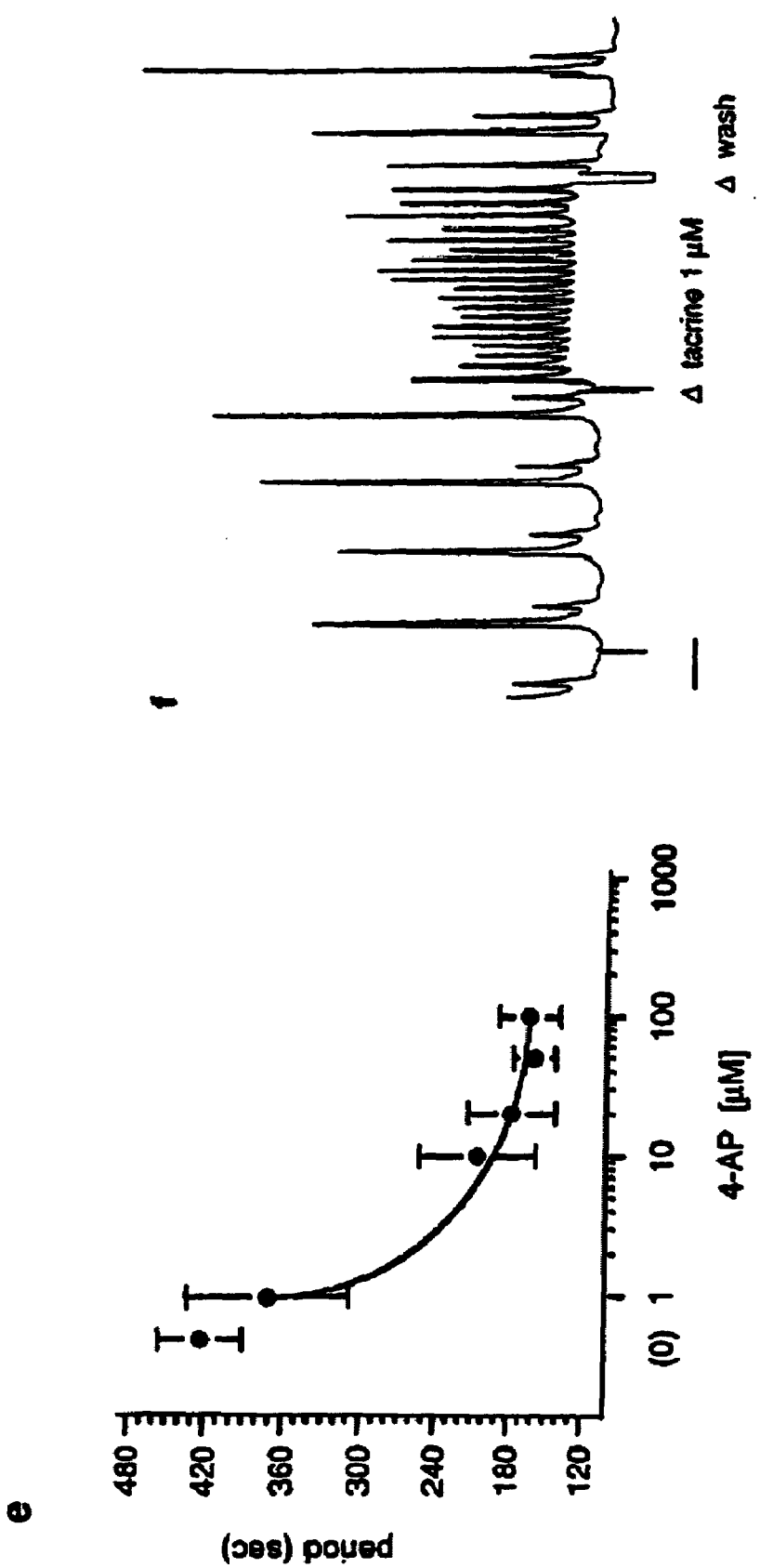
Figure 4:
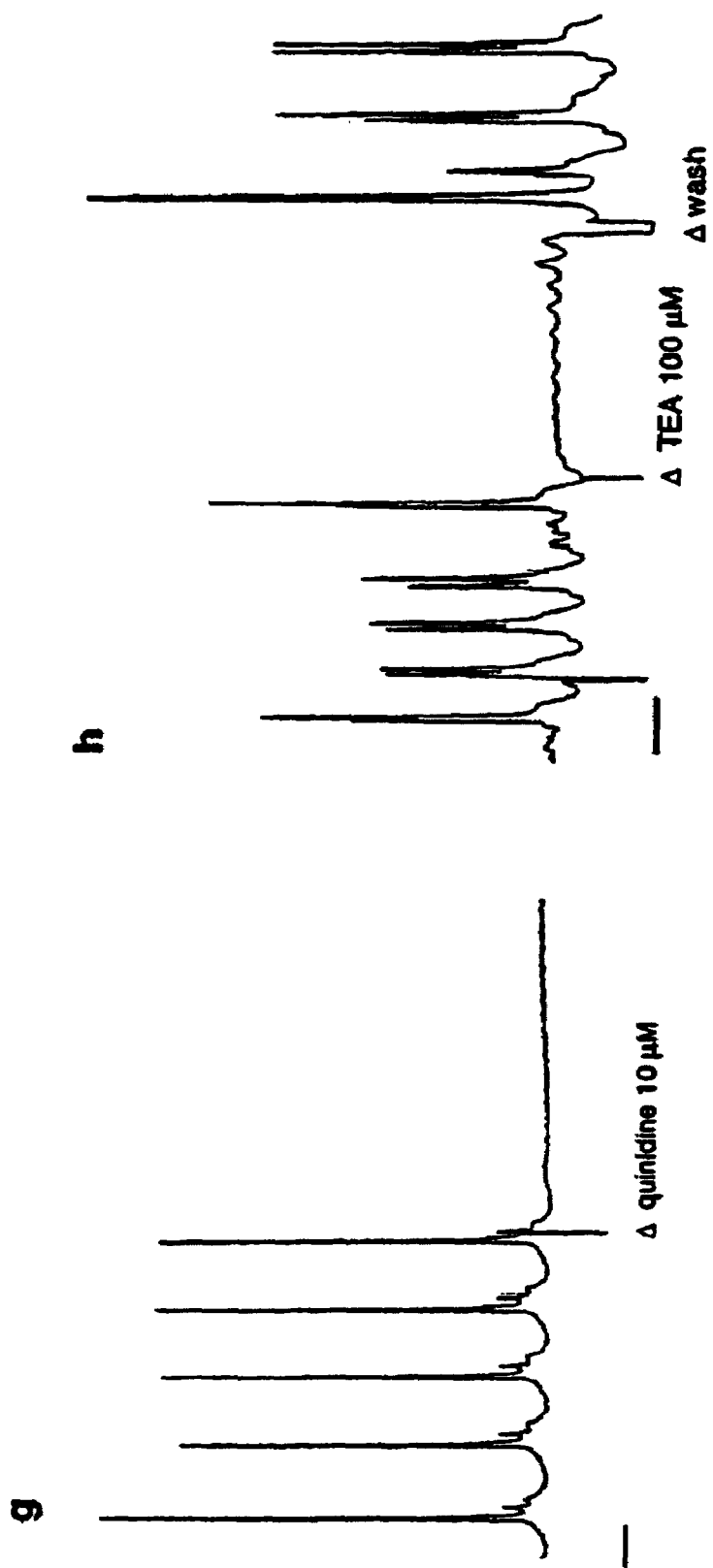

FIG. 4 shows the effect of voltage gated potassium blockers on cytoplasmic calcium oscillations. Representative traces of 117Y-aeq adult brains. Horizontal bar, 5 min. Dose responses for the blockers of voltage-gated potassium channel, (a) 4-AP, tacrine, (b) TEA, quinidine, (c) 4-AP is a blocker of the fast transient $I_A$(Shaker-like) current, (d) The Shaker mutant (Sh$^5$) is defective for an 4-AP sensitive sub-class of voltage-gated potassium channel-subunits, (e) effect of 4-AP on the period of the oscillations, (f) Tacrine and (g) quinidine block the delayed rectifier $I_K$ current, (h) TEA is described as blocking both $I_K$ and $I_{CF}$, the fast calcium-activated current.

Figure 5:
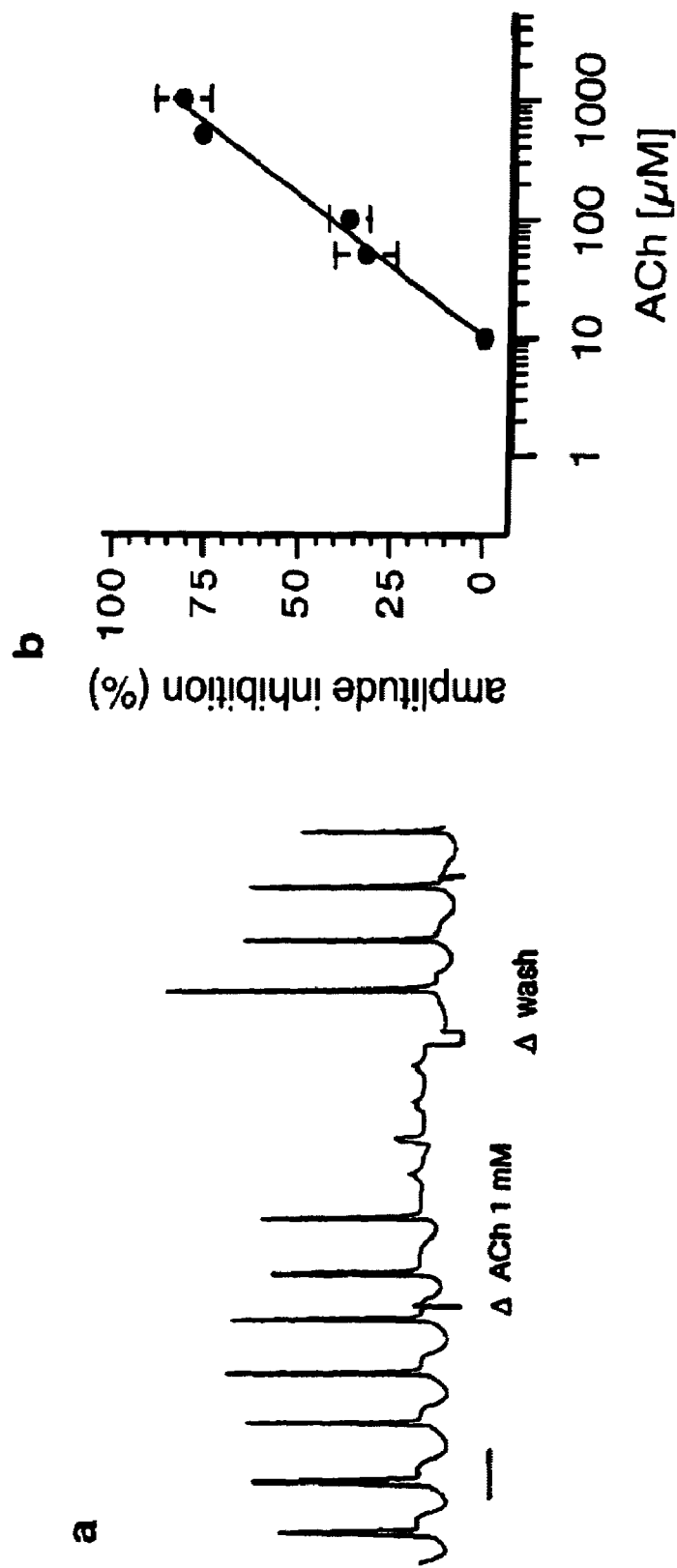
Figure 5:
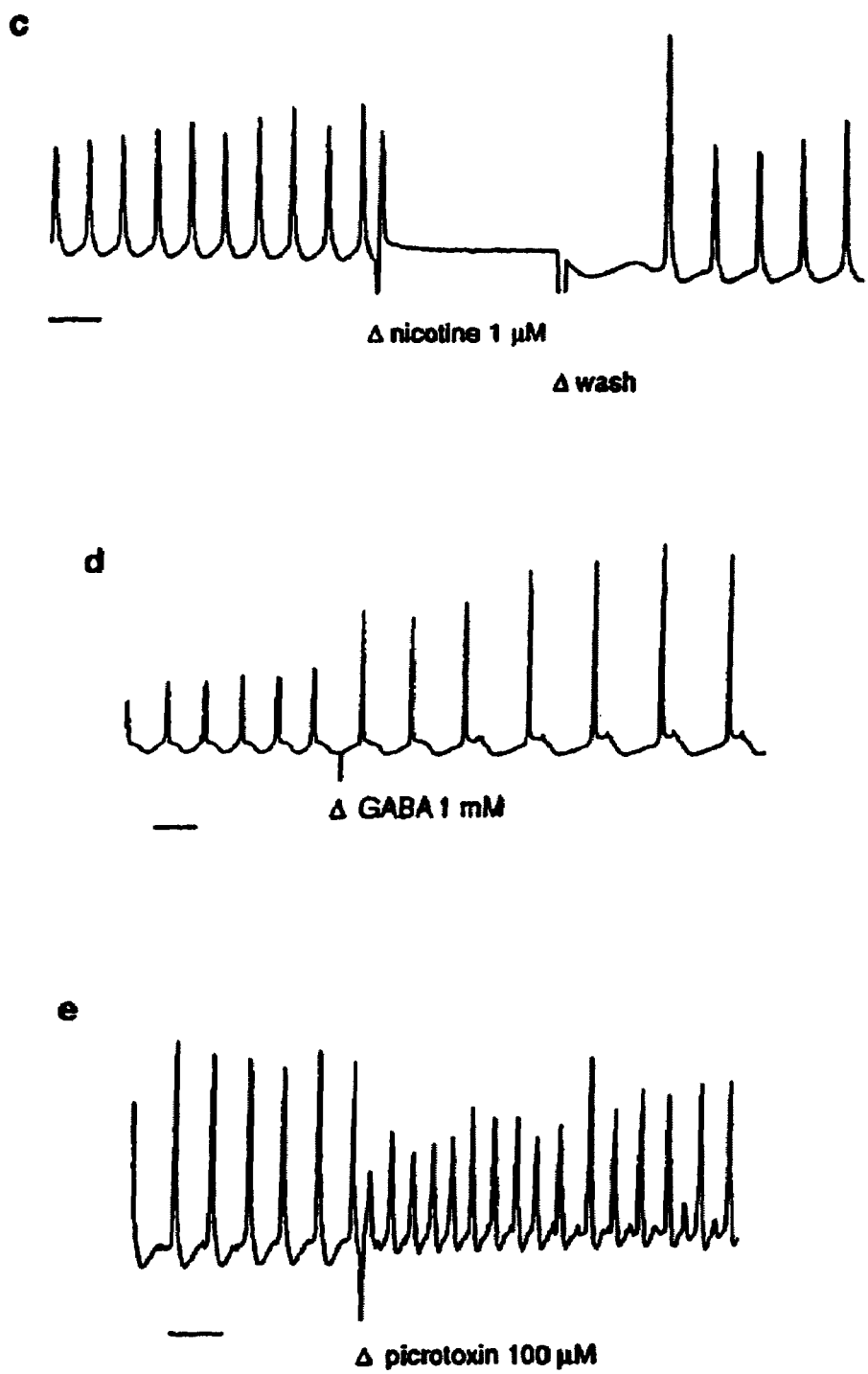
Figure 5:
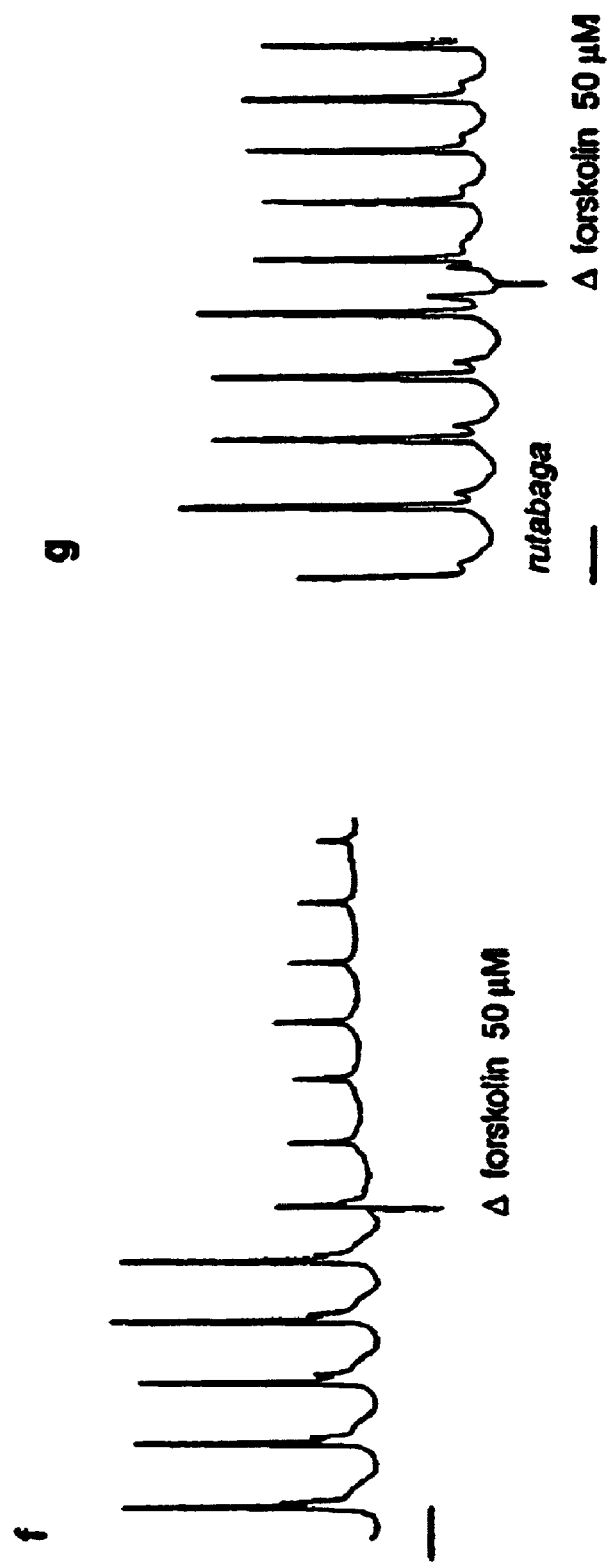

FIG. 5 shows the effect on calcium signalling of reagents active on neuro transmitter receptors and cAMP second messenger pathways. Representative traces of 117Y-aeq adult brains. Horizontal bar, 5 min Acetylcholine receptors pharmacology, (a) Reversible reduction of oscillation amplitude by acetyl choline (b) Dose response for acetyl choline, (c) Nicotine at 1 µM is sufficient for complete abolition of oscillation. Role of GABAergic neurons in calcium oscillations, (d) GABA increases both amplitude and period, (e) Picrotoxin, a GABA receptor antagonist, has the opposite effects. Effect on calcium signalling of reagents active on cAMP second messenger pathways, (f) Forskolin reduces oscillations amplitude in a wild type context, (g) but less effectively in the rutabaga mutant background (rut1). The rutabaga mutant is defective in a calcium-activated adenylyl cyclase.

MATERIAL AND METHODS

Generation of pUAST-Aequorin Flies

An apoaequorin cDNA was extracted from the plasmid pAQ2 (available from Molecular probes Inc. USA) by double digestion with SmaI and PstI, and inserted into similarly cleaved PBKS+ (available from Stratagene). Recleavage with NotI and KpnI allowed insertion into the similarly cleaved pUAST transformation vector (Brand and Perrimon, 1993), downstream of the five UAS$_G$ (GAL4-binding) sites, hsp70 TATA box and transcription start site. Germ-line transformed *Drosophila* were generated and two functionally equivalent lines, UAS$_G$-aeq30D and UASG-aeq49A, were obtained that have the transgene at the indicated cytogenetic locations (Rosay et al., 1997). Remobilisation was used to generate new insertions on the X chromosome, on a CyO balancer chromosome and on the third chromosome (see Table 1).

*Drosophila* Methods

The P{GAL4} lines described here arose from a screen described by Yang, et al. (1995; Table 1). GAL4 is a yeast transcription factor that is functional in *Drosophila*. Its pattern and timing of expression are dependent upon the genomic context of the inserted P[GAL4] element. GAL4 can be used to drive expression of secondary reporters linked to the GAL4-responsive promoter, UAS$_G$.

Hydroxyurea Ablation

HU ablation was performed according to deBelle and Heisenberg (1994). Newly hatched larvae (30+/−30 min after larval hatching) were fed a 4 hour pulse of heat-killed yeast suspension containing 50 mg/ml HU. Larvae were then transferred to standard medium without HU. Control insects were fed yeast only.

Luminometry

Brains were dissected under insect saline (Na$^+$, 132 mM; K$^+$, 20 mM; Ca$^{2+}$, 2 mM;Cl—, 158 mM; Mg$^{2+}$, 8.5 mM; H$_2$PO$_4$—, 4.3 mM; HCO$_3$—, 10.2 mM; glucose, 5 mM; pH adjusted to 7.0 with NaOH). Each luminometer trace represents a single brain floating freely in 100 µl of the above medium containing 2.5 µM hcp-coelenterazine (Molecular Probes). Luminescence was recorded in a Berthold Wallac LB9507 luminometer. Data were averaged over 5–15 sec. intervals. Luminescence is expressed in cps/10. Maximum background luminescence in the absence of GAL4 was 200–400 cps.

EXAMPLE 1

Endogenous Calcium Oscillation in the MBs

Different neuronal subtypes of the *Drosophila* mushroom bodies (MBs) are revealed by the P{GAL4} enhancer-trap system (Yang et al., 1995; Armstrong et al., 1998). Here, the present inventors have used the P{GAL4} system to drive cytosolic expression of aequorin (Rosay et al., 1997), a calcium-sensitive luminescent protein, within the MBs. Luminescence from an intact adult brain (103Y-aeq49A; see Table 1 for nomenclature) supplied with the aequorin co-factor, hcp-coelenterazine, arises predominantly from the MB calyces.

Cell-type specific expression of active aequorin with a pattern predicted from that of GAL4-directed beta galactosidase expression was confirmed in the context of P{GAL4} line 103Y, in which Kenyon cells of the adult mushroom bodies are clearly revealed. GAL4-directed beta galactosidase activity in a cryostat frontal section of the adult brain (103Y-lacZ) reveals the calyxes and cell-bodies of the paired mushroom bodies. GAL4-directed aequorin activity in a whole adult brain (103Y-aeq) bathed in Schneider's medium (Sigma) containing 2.5 µM hcp-coelenterazine; 3 min exposure to a Berthold Night Owl CCD camera (blue), superimposed on bright field image, clearly reveals the calyces.

FIG. 1a shows a luminometer trace of aequorin activity in a 103Y-aeq49A brain. The brain was removed from the head capsule, and bathed in simple insect saline (Ringer's solution) containing 2.5 µM hcp-coelenterazine. Robust oscillation of aequorin activity was observed with a mean period in the minute range. Oscillation reaches full amplitude by 30 min, consistent with the known time-dependence of the formation of active aequorin from apoaequorin and coelenterazine, and can last for 15 hours or more. The amplitude of the effect implies the superimposed luminescence of many KCs oscillating in synchrony.

Oscillations with the above characteristics were observed in the context of several P{GAL4} lines chosen on the basis of KC expression (e.g. FIGS. 1b,c). Oscillation can be observed in the living fly, not subject to surgical trauma except for a small slit in the head cuticle to enable coelenterazine entry (FIG. 1e).

Within any one brain, period, amplitude and waveform can remain effectively constant for hours. Oscillation occurs with a mean period of 324±13 sec (n=88), independent of P{GAL4}background and sex.

Experiments described hereafter have been carried out in the context of P{GAL4} lines 30Y and 117Y (FIGS. 1b,c; Yang et al., 1995; Tettamanti et al., 1997; Armstrong et al., 1998). Both reveal a large proportion of the adult KCs, and both provide oscillations of consistently high amplitude. In neither case are expression patterns entirely restricted to the mushroom bodies.

EXAMPLE 2

Hydroxyurea Ablation and Developmental Timing

Further evidence that oscillation occurs within KCs was provided by studies of GAL4-aeq flies in which the KCs had been selectively ablated. The 2000–3000 KCs of each *Drosophila* mushroom body arise from just four neuroblast precursors, which remain continuously active from mid-embryonic to late pupal stage. Just subsequent to larval hatching, all other neuroblasts (bar one) are quiescent, rendering KCs susceptible to ablation by pulse-feeding with hydroxyurea (HU). HU-treated animals survive to be healthy adults lacking 90% or more of the normal Kenyon cell complement, and are severely compromised in their associative olfactory learning abilities (deBelle and Heisenberg, 1994).

The effects of HU treatment were dramatic, as shown in FIG. 1d for line 30Y-aeq (n=8). Similar results were obtained for line 117Y-aeq.

Age at oscillation onset was examined in line 117Y-aeq, in which a significant proportion of the late larval and pupal KCs strongly express the GAL4 transcription factor. Oscillation was first detectable between 55 and 69 hours after puparium formation (APF), and was continuously present thereafter (compare FIGS. 1f and g). This is consistent with the time of origin of adult-specific mushroom body elements, the alpha and beta lobes.

EXAMPLE 3

Plasma Membrane Calcium Channels

Oscillation ceases following the removal of external calcium, either by buffer replacement (FIG. 2a), or by the addition of 1 mM EGTA (not shown). Oscillation returns with the addition of free external calcium. Cobalt has been reported to block all voltage-gated calcium channels in *Drosophila* brain membrane preparations (Pelzer et al., 1989). Here it is found to have a gradual dampening effect on oscillation in the 1–10 mM range (FIG. 2b).

Vertebrate L-type calcium channels are blocked by three chemically unrelated classes of compound; phenylalkylamines (e.g. verapamil), 1,4-dihydropyridines (e.g. nifedipine) and benzothiazapines (e.g. diltiazem), each of which binds to a different site on the alpha1 (calcium conducting) subunit. In contrast, *Drosophila* brain membrane preparations appear to contain independent calcium channels sensitive to phenylalkylamines (predominant and of unusually high affinity) and 1,4-dihydropyridines (e.g. Peltzer et al., 1989). Very little specific binding is detected for diltiazem. Honeybee KCs exhibit a calcium current that is affected by verapamil and nifedipine at relatively high concentrations (100 µM; Shäfer et al., 1994).

Present studies have found all three classes of agent significantly to reduce oscillation amplitude (FIGS. 2c–e) at or below concentrations used to block calcium currents in other *Drosophila* systems (Byerly and Leung, 1998; Gielow et al. 1995; Gu and Singh, 1995). Dose-response curves plotted on the basis of amplitudes measured before and after treatment, gives an $EC_{50}$ close to 3 µM for verapamil and 10 µM for diltiazem (FIG. 2f). None of the three agents had a consistent effect on oscillation frequency.

EXAMPLE 4

Effects of Various Agents on Calcium Level Oscillation
Sodium Channels

Tetrodotoxin (TTX) is a potent blocker of *Drosophila* voltage-gated sodium channels, and thus of neuronal electrical activity. TTX-sensitive sodium currents are exhibited by honeybee KCs (Shäfer et al., 1994). TTX causes cessation of oscillation within a few cycles of application (FIG. 3a), the precise timing depending upon the concentration used. After an intervening period, again dependent upon TTX concentration, oscillation resumes in the form of a series of spaced bursts of very high relative amplitude. The first peak in each burst is particularly high. Oscillation is eliminated by 1 µM veratridine, a sodium channel opener (FIG. 3b), accompanied by a sustained elevation of base-line calcium concentration.

Potassium Channels

Pharmacological criteria have been used to identify several voltage-activated potassium currents in *Drosophila*, the relative contributions of which depend upon cellular context. 4-aminopyridine (4-AP) blocks a fast transient voltage-gated current (IA-like) in cultured *Drosophila* larval CNS neurons (Solc and Aldrich, 1988), and more pertinently in cultured *Drosophila* larval KCs (Wright and Zhong, 1995) and in isolated honeybee adult KCs (Shäfer et al., 1994). Present studies find 4-AP to reduce oscillation amplitude in a dose-dependent manner (FIG. 4a; EC50~30 µM). There is also a dose-dependent reduction of oscillation period (FIG. 4e).

Non $I_A$-like *Drosophila* potassium channels all appear to be blocked by tetraethylammonium acetate (TEA; Gho and Mallert, 1986; Wu and Ganetzky, 1992). The present inventors find 100 μM TEA to eliminate oscillations (FIG. 4h). EC50 for TEA is ~70 μM (FIG. 4b). Tacrine and quinidine, blockers of delayed rectifying voltage-gated currents ($I_K$-like; Singh and Wu, 1989; Kraliz and Singh, 1997; Kraliz et al., 1997), even more potently reduce both oscillation amplitude and frequency (FIGS. 4f,g; EC50 for tacrine is approximately 1 μM, quinidine 2 μM). Honeybee KCs exhibit a delayed rectifier-type current that is only weakly sensitive to TEA, but that is blocked by 100 μM quinidine (Shäfer et al., 1994). Since each of the above three agents can modulate a range of other ion channels and/or other neuronally important molecules, these observations were followed with mutant studies as described below for 4-AP and Shaker.

The Shaker(Sh) locus defines a 4-AP sensitive sub-class of voltage-gated potassium channel a-subunits. Physiological effects of Sh include abnormal A-type potassium currents in embryonic myocytes, larval and pupal muscle, and a range of associated defects in neural activity and synaptic transmission (e.g. Haugland and Wu, 1990). The present inventors have examined the effects of the $Sh^5$ mutation. While oscillation did usually occur in a $Sh^5$ background (as many as 30% of brains gave no oscillation at all), it was 10-fold less sensitive to 4-AP than the $Sh^+$ control (FIGS. 4a,d).

Neurotransmitters and Modulators

Antenno-glomerular tract fibres (AGT-MB input elements) in several other insects species are cholinergic, and calcium imaging of cultured honeybee KCs has revealed the presence of receptors for acetylcholine (ACh) and nicotine that are blocked by alpha-bungarotoxin (Bicker and Kreissl, 1994). ACh gradually reduces oscillation amplitude in a dose dependent and reversible manner (FIGS. 5a,b). Nicotine was much more potent, 1 μM being sufficient for complete abolition of oscillation (FIG. 5c).

KC dendrites also receive inhibitory, GABAergic, input via recurrent extrinsic elements (Bicker et al., 1985; Gronenberg, 1987). 1 mM GABA increases both amplitude and period (FIG. 5d). Picrotoxin, a GABA receptor antagonist, has the opposite effects (FIG. 5e).

cAMP Pathway

Forskolin, an activator of adenylylcyclase, reduces oscillation amplitude with little effect on period (FIG. 5f). 1 mM dibutyryl cAMP was ineffective, however. The rutabaga gene encodes a calcium-activated adenylyl cyclase that is highly expressed in the mushroom bodies, and that has a demonstrated role in *Drosophila* learning and memory (Han et al., 1992). Oscillation in a $rut^1$ background was largely insensitive to forskolin (FIG. 5g).

TABLE 1

| Line | Chromosomal Location | Reference |
| --- | --- | --- |
| UAS$_c$-aeqA1 | X chromosome | This study |
| UAS$_c$-aeq30D | 30D | Rosay et al., 1997 |
| UAS$_c$-aeq49A | 49A | Rosay et al., 1997 |
| UAS$_c$-aeqA8 | CyO | This study |
| UAS$_c$-aeqA10 | chromosome 3 | This study |
| UAS$_c$-aeqA14 | chromosome 3 | This study |
| P{GAL4}30Y | 70E | Yang et al., 1995 |
|  |  | Armstrong et al., 1997 |
| P{GAL4}103Y | 2D | Tettamanti et al., 1997 |
| P{GAL4}117Y | 34C | Tettamanti et al., 1997 |
|  |  | Armstrong et al., 1998 |

Testing of Further Compounds/Mutations Using the Present Assay

Table 2 lists other compounds that affect calcium oscillations. These include several known insecticides as well as several compounds of clinical therapeutic use. The amnesiac gene encodes for peptides whose activity may be, at least in part, thought to modulate the cAMP pathway.

TABLE 2

| Targets & Usage | Compounds | Effect on neural activity |
| --- | --- | --- |
| a. Insecticides | | |
| Respiratory chain | | |
| NDH | Rotenon | BI,AD |
| SDH | Thiapronil | BI |
| Uncoupler | CCCP | BI,AD |
| Neurotransmission | | |
| ACh esterase | Paraoxon | AD,FI |
| GABAA-R channel blocker | Fipronil | AD,FI |
| Glutamate (Cl—) R agonist | Ivermectin B1a | BI,AD |
| Nicotinic ACh R agonist | Imidacloprid | AD |
| | Nithiazine | AD |
| | Nicotine | AD |
| | Spinosad | AD |
| Sodium channel opener | Veratrine | BI |
| | Veratridine | BI |
| Sodium channel modulator | Resmethrin | AD,FI |
| b. Human therapeutic | | |
| ACh esterase, Alzheimer | Tacrine | AD,FI |
| Anaesthesia, pain | Morphine | AD,FI |
| Antileukemia antineoplastic | Harringtonine | AD |
| Ocular peri-operative drugs | Acetylcholine | AD |
| Hypertension, angina | Nefedipine | AD |
| | Verapamil | AD |
| | Diltiazem | AD |
| Tachycardias, arrhythmias | Quinidine | AD,FI |
| Nausea, psychoses | Trifluoperazine | AD,BD |
| c. Others | | |
| Adenylyl cyclase | Forskolin | AD |
| Calcium ATPase | Thapsigargin | AD |
| Calcium channel antagonist | Cobalt | AD |
| Calmodulin antagonist | W7 | AD |
| GABAA-R channel agonist | GABA | AI,FD |
| | Muscimol | AI,FD |
| GABAA-R channel blocker | Pierotoxin | AD,FI |
| Nicotinic aCh R antagonist | Dihydro-β-erythroidine | AD,FD |
| | Mecamylamine | AD,FD |
| Potassium channel antagonist | 4-aminopyridine | AD,FI |
| Sodium channel antagonist | TEA | AD,FI |
| | Tetrodotoxin | AD |

| Mutations | Gene product | Effect on neural activity |
| --- | --- | --- |
| rutabaga | Adenylate cyclase | Forskolin insensitive |
| amnesiae | Neuropeptide | AI |
| Shaker | Potassium channel | 4-aminopyridine |

Abbreviations: A = amplitude, F = frequency, B = basal level, D = decrease, I = increase, ACh = acetylcholine, R = receptor.

REFERENCES

Armstrong, J., and K. Kaiser, 1997, Enhancer-trap studies of the *Drosophila* brain, in L. M. Houdebine, ed., Transgenic Animals: Generation and Use, Harwood Academic Publishers, p. 365–370.

Armstrong, D. J., deBelle, J. S., Wang Z. and Kaiser, K. (1998) Metamorphosis of the mushroom bodies; large scale rearrangements of the neural substrates for associative learning and memory in *Drosophila*. Learning and Memory (in press).

Bicker, G. and Kreissl, S. (1994) Calcium imaging reveals nicotinic acetylcholine receptors on cultured mushroom body neurons. J. Neurophysiol. 71, 808–810.

Bicker, G., Schafer, S. and Kingan, T. G. (1985) Mushroom body feedback interneurones in the honeybee show GABA-like immunoreactivity. Brain Res. 1985 360, 394–397.

Brand, A. H., and Perrimon, N. (1993). Targeted gene expression as a means of altering cell fates and generating dominant phenotypes. Development 118,401–415.

Byerly L. and Leung, H. T. (1988) Ionic currents of *Drosophila* neurons in embryonic cultures. J. Neurosci. 8, 4379–4393.

Cobbold, P. H., and Rink, T. J. (1987) Fluorescence and bioluminescence measurement of cytoplasmic free calcium. Biochem J. 248, 313).

Dani, J., and S. Smith, 1995, The triffering of astrocytic calcium waves by NMDA-induced neuronal activation: Ciba Found Symp., 188, 195–205.

deBelle J. S., and Heisenberg, M. (1994). Associative odor learning in *Drosophila* abolished by chemical ablation of mushroom bodies. Science 236,692.

Duffy, S., and B. MacVicar, 1995, Adrenergic calcium signalling in astrocyte networks within the hippocampal slice: J. Neurosci., 15,5535–5550.

Gho, M. and Mallart, A. (1986) Two distinct calcium activated K+ currents in larval muscle fibers of *Drosophila*. Pfluegers Arch. 407, 526–533.

Gielow, M. L., Gu, G-G. and Singh, S. (1995) Resolution and pharmacological analysis of the voltage-dependent calcium channels of *Drosophila* larval muscles. J. Neurosci. 15, 6085–6093.

Grapengiesser E, Gylfe E and Hellman (1988) Glucose-induced oscillations of cytoplasmic Ca2+ in the pancreatic beta-cell. B Biochem Biophys ResCommun 1988 151(3):1299–1304.

Grapengiesser E (1996) Glucoseinduces cytoplasmic Na+ oscillations in pancreatic beta-cells. Biochem Biophys Res Commun 1996 226(3):830–835.

Gronenberg, W. (1987) Anatomical and physiological properties of feedback neurons of the mushroom bodies in the bee brain. Exp. Biol. 46, 115–125.

Gu, G-G. and Singh, S. (1995) Pharmacological analysis of heartbeat in *Drosophila*. J Neurobiol. 28, 269–280.

Han, P-L., Levin, L. R., Reed, R. R., and Davis, R. L. (1992). Preferential expression of the *Drosophila* rutabaga gene in mushroom bodies, neural centers for learning in insects. Neuron 9,619–627.

Haugland, F. N. and Wu, C. F. (1990) A voltage-clamp analysis of gene-dosage effects of the Shaker locus on larval muscle potassium currents in *Drosophila*. J. Neurosci. 10, 1357–1371.

Kraliz, D. and Singh, S. (1997) Selective blockade of the delayed rectifier potassium current by tacrine in *Drosophila*. J. Neurobiol. 32, 1–10.

Kraliz, D., Bhattacharya, A. and Singh, S. (1997) Blockade of the delayed rectifier potassium current in *Drosophila* by quinidine and related compounds. J. Neurogenet. (in press).

Miyawaki A, Llopis J, Heim R, McCaffery J M, Adams J A, Ikura M, Tsien R Y (1997) Fluorescent indicators for CA2+ based on green fluorescent proteins and calmodulin. Nature, 388(6645):882–887).

Ogden, D., 1996, Intracellular calcium release in central neurones: seminars in Neurosc., 8, 281–291.

Pelzer, S., Barhanin, J., Pauron, D., Trautwein, W., Lazdunski, M. and Pelzer, D. (1989) Diversity and novel pharmacological properties of Ca2+ channels in *Drosophila* brain membranes. EMBO J. 8, 2365–2371.

Rohr, S., and Salzberg, B. M. (1994) Multiple site optical recording of transmembrane voltage (MSORTV) in patterned growth heart cell cultures: assessing electrical behavior, with microsecond resolution, on a cellular and subcellular scale. Biophys. J. 67, 1301.

Romoser V A, Hinkle P M, Persechini A(1997) Detection in living cells of Ca2+-dependent changes in the fluorescence emission of an indicator composed of two green fluorescent protein variants linked by a calmodulin-binding sequence. A new class of fluorescent indicators. J Biol Chem 1997 272(20): 13270–13274.

Rosay, P., Davies, S., Yu, Y., Sozen, M. A., Kaiser, K. and Dow, J.A.T. (1997) Cell-type specific calcium signalling in a *Drosophila* epithelium. J. Cell. Sci. 110, 1683–1692.

Seymour-Laurent, K., and M. Barish, 1995, Inositol 1,3,4-trisphosphate and ryanodine receptor distributions and patterns of acetyl choline- and caffeine-induced calcium release in cultured mouse hippocampal neurons: J. Neurosci., 15, 2592–2608.

Shafer, S., Rosenboom, H. and Menzel, R. (1994) Ionic currents of Kenyon cells from the mushroom body of the honeybee. J. Neurosci. 14, 4600–4612.

Singh, S. and Wu, C-F. (1989) Complete separation of four potassium currents in *Drosophila*. Neuron 2, 1325–1329.

Solc, C. K. and Aldrich, R. W. (1988) Voltage-gated potassium channels in larval CNS neurons of *Drosophila*. J. Neurosci. 8, 2556–2570.

Tettamanti, M., Armstrong, J. D., Endo, K., Yang, M. Y., Furukubo-Tokunaga, K., Kaiser, K. and Reichert, H. (1997) Early development of the *Drosophila* mushroom bodies, brain centres for associative learning and memory. Dev. Genes and Evol. 207, 242–252.

Wang X and Gruenstein E I (1997) Mechanism of synchronized Ca2+ oscillations in cortical neurons. Brain Res 767(2):239–249.

Woods, N., K. Cuthbertson, and P. Cobbold, 1986, Repetitive transient rises in cytoplasmic free calcium in hormone-stimulated hepatocytes: Nature, 319, 600–602.

Wright, N. J. and Zhong, Y. (1995) Characterization of K+ currents and the cAMP-dependent modulation incultured *Drosophila* mushroom body neurons identified by lacZ expression. J. Neurosci. 15, 1025–1034.

Wu, C-F. and Ganetzky, B. (1992) Neurogenetic studies of ion channels in *Drosophila*. In 'Ion Channels' Vol. 3 (ed. T. Narahashi), Plenum Press, New York, pp. 261–314.

Yang, M. Y., Armstrong, D. J., Vilinsky, I., Strausfeld, N. J. and Kaiser, K. (1995) Subdivision of the *Drosophila* mushroom bodies by enhancer-trap expression patterns. Neuron 15, 45–54.

What is claimed is:

1. An in situ method of screening a compound for a pharmacological activity which comprises:
   a) detecting an initial endogenous oscillation pattern of neural activity in insect or arachnid brain tissue;
   b) adding the compound to the brain tissue and detecting a resulting pattern of neural activity; and
   c) observing the pharmacological activity of the compound on neural activity by comparing the initial endogenous oscillation pattern of intracellular neural activity with the resulting pattern of neural activity.

2. The method according to claim 1 wherein the neural activity is detected as a pattern of calcium oscillation.

3. The method according to claim 2 wherein the method of detecting said pattern of neural activity comprises expressing apoaequorin in the brain tissue being tested.

4. The method according to claim 3 wherein the apoaequorin is expressed transgenically.

5. The method according to claim 3 wherein the apoaequorin is derived from an aequorin gene under GAL4-control.

6. The method according to claim 3 wherein intracellular calcium concentration is detected by the addition of coelenterazine to brain tissue expressing apoaequorin.

7. The method according to claim 3 wherein detecting of said pattern of neural activity is carried out using a CCD camera, luminometer, or other suitable detection means.

8. The method according to claim 1 wherein said pattern of neural activity is detected directly or indirectly by a) a method that monitors intracellular calcium concentration; b) a method that monitors the operation of intracellular calcium signaling pathways; c) a method that monitors the operation of other types of signaling pathway; or d) a method that monitors neural electrical potentials.

9. The method according to claim 8 part a) comprising the use of fluorescent probes which show a spectral response upon binding calcium and detecting changes in intracellular free calcium concentrations using fluorescence microscopy, flow cytometry or fluorescence spectroscopy.

10. The method according to claim 9 wherein the fluorescent probe is a so-called cameleon which comprises a tandem fusion of a blue-, or a cyan-emitting mutant of green fluorescent protein (GFP), calmodulin, the calmodulin-binding peptide M13, and an enhanced green-, or yellow-emitting GFP.

11. The method according to claim 8 part d) comprising the use of potentiometric optical probes.

12. The method according to claim 1 wherein detection is performed on a live organism.

13. The method according to claim 1 wherein detection is performed on brain tissue which has been dissected from an organism.

14. The method according to claim 1 wherein the addition of a compound results in a cessation of the neural activity for a period of time, variation in the pattern of activity or both.

15. The method according to claim 14 wherein the variation is an increase/decrease in an amplitude of oscillation or alteration in the frequency and/or wave pattern observed.

16. The method according to claim 14 for ascertaining if the compound acts in a agonistic or antagonistic manner.

17. The method according to claim 1 wherein the oscillation pattern is synchronous.

18. A method for detecting a calcium signaling mutant insect or arachnid, the method comprising detecting a pattern of endogenous intracellular calcium oscillation in brain tissue of a test insect or arachnid and comparing this with a pattern of endogenous intracellular calcium oscillation in neural tissue of a non-mutant insect or arachnid.

19. An in situ method of screening a compound for a pharmacological activity which comprises:
   a) detecting an initial endogenous oscillation pattern of neural activity in insect brain tissue;
   b) adding the compound to the brain tissue and detecting a resulting pattern of neural activity; and
   c) observing the pharmacological activity of the compound on neural activity by comparing the initial endogenous oscillation pattern of intracellular neural activity with the resulting pattern of neural activity.

20. An in situ method of screening a compound for a pharmacological activity which comprises:
   a) detecting an initial endogenous oscillation pattern of neural activity in *Drosophila* brain tissue;
   b) adding the compound to the brain tissue and detecting a resulting pattern of neural activity; and
   c) observing the pharmacological activity of the compound on neural activity by comparing the initial endogenous oscillation pattern of intracellular neural activity with the resulting pattern of neural activity.

21. An in situ method of screening a compound for a pharmacological activity which comprises:
   a) detecting an initial endogenous oscillation pattern of neural activity in insect or arachnid excitable brain tissue in intact preparations;
   b) adding the compound to the excitable brain tissue and detecting a resulting pattern of neural activity; and
   c) observing the pharmacological activity of the compound on neural activity by comparing the initial endogenous oscillation pattern of intracellular neural activity with the resulting pattern of neural activity.

* * * * *